US009029322B2

(12) United States Patent
Ratan et al.

(10) Patent No.: US 9,029,322 B2
(45) Date of Patent: May 12, 2015

(54) COMPOUNDS FOR ENHANCING P21 EXPRESSION AND METHODS OF USE THEREOF

(75) Inventors: Rajiv R. Ratan, Scarsdale, NY (US); Brett C. Langley, White Plains, NY (US); Brian S. Ko, Scarsdale, NY (US)

(73) Assignee: Cornell University, Ithaca, NY (US)

( * ) Notice: Subject to any disclaimer, the term of this patent is extended or adjusted under 35 U.S.C. 154(b) by 626 days.

(21) Appl. No.: 12/663,091

(22) PCT Filed: Jun. 5, 2008

(86) PCT No.: PCT/US2008/007168
§ 371 (c)(1),
(2), (4) Date: Mar. 22, 2010

(87) PCT Pub. No.: WO2008/150550
PCT Pub. Date: Dec. 11, 2008

(65) Prior Publication Data
US 2010/0167993 A1    Jul. 1, 2010

Related U.S. Application Data

(60) Provisional application No. 60/933,366, filed on Jun. 5, 2007.

(51) Int. Cl.
| | |
|---|---|
| *A61K 38/00* | (2006.01) |
| *A61K 38/28* | (2006.01) |
| *A61P 3/10* | (2006.01) |
| *A61P 7/12* | (2006.01) |
| *C12Q 1/68* | (2006.01) |
| *A01N 43/42* | (2006.01) |
| *A61K 31/44* | (2006.01) |
| *A01N 43/40* | (2006.01) |
| *A01N 43/16* | (2006.01) |
| *A61K 31/35* | (2006.01) |
| *A01N 37/12* | (2006.01) |
| *A01N 37/44* | (2006.01) |
| *A61K 31/195* | (2006.01) |
| *A01N 47/28* | (2006.01) |
| *A61K 31/17* | (2006.01) |
| *A01N 57/00* | (2006.01) |
| *A61K 31/675* | (2006.01) |
| *C07K 14/47* | (2006.01) |
| *G01N 33/50* | (2006.01) |

(52) U.S. Cl.
CPC ........ *C07K 14/4738* (2013.01); *G01N 33/5041* (2013.01)

(58) Field of Classification Search
CPC .............. G01N 33/5041; C07K 14/4738
USPC .......... 514/9, 345, 182, 283, 456, 596, 562; 435/6
See application file for complete search history.

(56) References Cited

U.S. PATENT DOCUMENTS 5,994,061 A        11/1999   Tam et al.
2002/0132845 A1*   9/2002    Miller et al. .................. 514/458

FOREIGN PATENT DOCUMENTS

WO      WO9804291       2/1998
WO      WO2006009836 A2 1/2006
WO      WO 2007048004 A2 * 4/2007

OTHER PUBLICATIONS

Di Giovanni, Simone. (2006). "Regeneration following spinal cord injury, from experimental models to humans: where are we?". Expert Opin. Ther; Targets., 10(3): 363-376.*
Chaoyong Ma (2004). "Animal Models of Disease." Modern Drug Discovery, 30-36.*
Danielle Simmons. (2008). "The use of Animal Models in Studying Genetic Disease: Transgenesis and Induced Mutation". Retrieved on Jul. 24, 2013. Retrieved from internet <URL: http://www.nature.com/scitable/topicpage/the-use-of-animal-models-in-studying-855>.*
Cakir et al (2003) "Neuroprotective effect of N-acetylcysteine and hypothermia on the spinal cord ischemia-reperfusion injury." Cardiovascular Surgery, 11(5): 375-379 (abstract only). Retrieved on Jul. 30, 2013. Retrieved from the internet <URL:http://www.ncbi.nlm.nih.gov/pubmed/12958548>.*
Liu et al (1999) "Induction of cyclin-dependent kinase inhibitors and G1 prolongation by the chemopreventive agent N-acetylcysteine." Carcinogenesis, 20(9): 1869-1872.*
Shanks et al. (2009). "Review: Are Animal Models Predictive for Human?" Philosophy, Ethics, and Humanities for Medicine, 4(2), 1-20.*
Haddad et al (2006) "Novel antiproliferative flavanoids induce cell cycle arrest in human prostate cancer cell lines." Prostate Cancer and Prostatic Diseases, 9: 68-75.*
Nakano et al., "Butyrate Actives the WAF1/Cip1 Gene Promoter Through Sp1 Sites in a p53-negative Human Colon Cancer Cell Line", Journal of Biological Chemistry, vol. 272, No. 35, pp. 22199-22206 (1997).
Zhou, et al., "Control of Mammary Tumor Cell Growth in vitro by Novel Cell Differentiation and Apoptosis Agents", Breast Cancel Research and Treatment, 75: 107-117 (2002).
Xiao et al., "p300 Collaborates with Sp1 and Sp3 in p21waf1/cip1 Promoter Activation Induces by Histone Deacetylase Inhibitor", The Journal of Biological Chemistry, vol. 275, No. 2, pp. 1371-1376 (2000).
Huang et al., "Activation of the p21waf1/cip1 Promotor Independent of p53 by the Histone Deacetylase Inhibitor Suberoylanilide hydroxamic Acid (SAHA) Through the Sp1 Sites", Oncogene, 19, 5712-5719 (2000).

(Continued)

Primary Examiner — Anoop Singh
Assistant Examiner — Doan Phan
(74) Attorney, Agent, or Firm — Hoffmann & Baron, LLP

(57) ABSTRACT

The present invention relates to a method for identifying a drug candidate for enhancing expression of p21cip1/waf1 in a human patient suffering from a medical condition that can be treated by enhancing expression of p21Cϕ1/waf1. The method includes (a) providing a cell line comprising a nucleic acid sequence that comprises a p21cip1/waf1 promoter operationally ligated to a reporter domain; (b) exposing the cell line to a compound; and (c) identifying a compound that induces expression of the reporter domain. The compound that induces expression of the reporter domain is a drug candidate for treating a medical condition that can be treated by enhancing expression of p21cip1/waf1.

13 Claims, 7 Drawing Sheets

(56) References Cited

OTHER PUBLICATIONS

Evdokiou et al., "Identification of a Novel Calcitonin-Response Element in the Promoter of the Human p21 waf1/cip1 Gene", Journal of Molecular Endocrinology, 25, 195-206 (2000).

Lagger, et al., "The Tumor Suppressor p53 and Histone Deacetylase 1 are Antagonistic Regulators of the Cyclin-Dependent Kinase Inhibitor p21/WAF1/CIP1 Gene", Molecular and Cellular Biology, vol. 23, No. 8, pp. 2669-2679 (2003).

Hsu, et al., "Acacetin-Induced Cell Cycle Arrest and Apoptosis in Human Non-Small Cell Lung Cancer A549 Cells", Cancer Letters, 212, pp. 53-60 (2004).

Gui et al., "Histone Deacetylase (HDAC) Inhibitor Activation of p21waf1 Involves Changes in Promoter-associated Proteins, Including HDAC1", PNAS, vol. 101, No. 5, pp. 1241-1246 (2004).

Langley et al., "RemodelingChromatin and Stress Resistance in the Central Nervous System: Histone Deacetylase Inhibitors as Novel and Broadly Effective Heuroprotective Agents", Current Drug Targets, CNS & Neurological Disorders, 4, pp. 41-50 (2005).

Nargi et al., "p53-Independent Inhibition of Proliferation and p21 Waf1/cip1-Modulated Induction of Cell Death by the Antioxidants N-Acetylcysteine and Vitamin E1", Neoplasia, vol. 1, No. 6, pp. 544-556 (1999).

Szuts et al., "Cell Cycle Arrest at the Initiation Step of Human Chromosomal DNA Replication Causes DNA Damage", Journal of Cell Science, vol. 117, No. 21, pp. 4897-4908 (2004).

Zhou et al., "Human Bronchial Smooth Muscle Cell Lines Show a Hypertrophic Phenotype Typical of Severe Asthma" AJRCCM, pp. 1-52 (2003).

\* cited by examiner

FIG. 1A

GenBank accession No. U24170

```
   1 ggatccctgt agagatgctc aggctgctga ggagggcgcg gtgcttggtc tctatgaata
  61 cgatgaccta aagcaaaaaa agaagatggc tatgtcggtg aagctctatg gaactgggga
 121 tcaggaggcc tggcagaaag gagtcctgtt tgcttctggg cagaacttgg catgatggag
 181 acgccagcca gcgagatgat gccaaccaga tttgccgaaa ttattgagaa gaatctcaaa
 241 agccgctagt agtaaaccga gtttcatatc agacccaggt cttggattga ggaacaggca
 301 atgggatcat tcctcagtgt ggccaaagga tctgacgagc cctcagtctt cttggaaatt
 361 cactacatag gcagcccaa tgcagacaaa ccacccttg tttgttggga aaggaattac
 421 ctttgacagt ggtggtatct ccatcaaggc ttctgcaaat atggacctca tgagggccga
 481 catgggagga gctacaacta tatgctcagc cattgtgtct gctgcaaatc tcagtttgcc
 541 cattaatatt ataggtctgg ccctctgtg aaaacatgcc cagcggcaag gccaacaagc
 601 tggggatgtt gttagagcca ggaacaggaa gaccatccag gttggtaaca ctgatgctga
 661 ggggaggctc atactggctg atgcgctctg ttacgtgcac acatttaacc cgaaggtcat
 721 cctcaatgcc accaccttaa caggtgtcat agatgtagct ttggggtcag gtgccactgg
 781 ggtctttacc aattcatcct ggctctggaa caagctcttc gaggccagca ttgaaacagg
 841 ggaccgtgtc tggaggatgc ctctcttcaa acattgtaca agacaggttg tagattgcca
 901 gctggctgat gttaacaaca ttggaaaata tagatctgcg ggagcatgta catctgcggc
 961 attcctgaaa gaattcgtga ctcatcctaa gtgggcacat ttagacatag caggtgtgat
1021 gaccaacaaa gatgaggttc cctatctatg gaaaggcatg accgggaggc ccacaaggac
1081 tctcatagag ttcttacttc gtttcagtca agacaatgct tagttcagat actcaaaaaa
1141 tgtcttcact ctgtcttaaa ttggacagtt gaagttaaaa ggttttttgaa tgaatggatg
1201 aaaatatttt aaaggaggca atttatattt aaaaatgtag aacacaatga aatttttatg
1261 ccttgatttt tttttcattt tacacaaaga tttatatatt ttttttttga gacggagtct
1321 cactctgtca cccaggctgg agtgcaggtg gcatgatctc agctcactgc aacctccgcc
1381 tcctaggttc aagcgattct cccacctcag ccacctgaat acctgggact acaggtgccc
1441 accaccatgc ccggctgatt tttgtatttt taatggagac ggggtttcac catattggcc
1501 aggctggtct caaaactcct gaccctgtga tctgcccgcc tcggcctccc aaagtgctgg
1561 gattacaggc gtaaaccacc acgcccggcc agtatatatt tttaattgag aagcaaaatt
1621 gtacttcaga tttgtgatgc taggaacatg agcaaactga aaattactaa ccacttgtca
1681 gaaacaataa atccaacttt ttgtgcaaaa aaaaaaaata caaatattag ctgggcatgg
1741 tggtgcatgc ctgtaatccc agctactcgg gaggctgagg cagaattgct tgaacctggg
1801 aggcggagac tgcagtgagc tgagattgtg ccactgctga cttttgtctca aaaaacaaaa
1861 caaaacaaaa aaacaaaatg aaaacaaaaa gccagggctg cctctgctca ataatgttct
1921 atctttgttc cgcctcttct ctggggtctc acttcttggg agcctgtgtg aaggtgaatt
1981 cctctgaaag ctgactgccc ctatttggga ctccccagtc tctttctgag aaatggtgac
2041 attgttccca gcacttcctc tccttccta ggcagcttct gcagccacca ctgagccttc
2101 ctcacatcct ccttcttcag gcttgggctt tccacctttc accattcccc tacccatgc
2161 tgctccaccg cactctgggg aggggctgg actgggcact cttgtccccc aggctgagcc
2221 tccctccatc cctatgctgc ctgcttccca ggaacatgct gggcagcag gctgtggctc
2281 tgattggctt tctgccatc aggaacatgt cccaacatgt tgagctctgg catagaagag
2341 gctggtggct attttgtcct tgggctgcct gttttcaggg aggaagggga tggtaggaga
2401 caggagacct ctaaagaccc caggtaaacc ttagcctctt actctgaaca gggtatgtga
```

FIG. 1B

```
2461 tctgccagca ggatccttgc gacagggctg ggatctgatg catgtgtgct tgtgtgagtg
2521 tgtgctggga gtcagattct gtgtgtgact tttaacagcc tgctcccttg ccttcttcag
2581 ggcagaagtc ctcccttaga gtgtgtctgg gtacacattc aagtgcatgg ttgcaaactt
2641 ttttttttaa agcactgaat agtactagac acttagtagg tacttaagaa atattgaatg
2701 tcgtggtggt ggtgagctag aagttataaa aaaaattctt tcccaaaaac aacaacaaaa
2761 agaattattt cattgtgaag ctcagtacca caaaaattca ttacaataat tcattacaag
2821 cctttattaa aaaaaatttt ctccccaaag taaacagaca gacaatgtct agtctatttg
2881 aaatgcctga aagcagaggg gcttcaaggc agtgggagaa ggtgcctgtc ctctgctgga
2941 catttgacaa ccagcccttt ggatggtttg tatgtatagg agcgaaggtg cagacagcag
3001 tggggcttag agtggggtcc tgaggctgtg ctgtggccct tctggggttt agccacaatc
3061 ctggcctgac tccagggcga ggcaggccaa gggggtctgc tgctgtgtcc tcccacccct
3121 acctgggctc ccatcccccac agcagaggag aaagaagcct gtcctccccg aggtcagctg
3181 cgttagagga agaagactgg gcatgtctgg gcagagattt ccagactctg agcagcctga
3241 gatgtcagta attgtagctg ctccaagcct gggttctgtt tttcagtggg atttctgttc
3301 agatgaacaa tccatcctct gcaattttt aaaagcaaaa ctgcaaatgt ttcaggcaca
3361 gaaaggaggc aaaggtgaag tccaggggag gtcaggggtg tgaggtagat gggagcggat
3421 agacacatca ctcatttctg tgtctgtcag aagaaccagt agacacttcc agaattgtcc
3481 tttatttatg tcatctccat aaaccatctg caaatgaggg ttatttggca tttttgtcat
3541 tttggaacca cagaaataaa ggatgacaag cagagagccc cggcaggag gcaaaagtcc
3601 tgtgttccaa ctatagtcat ttctttgctg catgatctga gttaggtcac cagacttctc
3661 tgagccccag tttccccagc agtgtatacg ggctatgtgg ggagtattca ggagacagac
3721 aactcactcg tcaaatcctc cccttcctgg ccaacaaagc tgctgcaacc acagggtt
3781 cttctgttca ggtgagtgta gggtgtaggg agattggttc aatgtccaat tcttctgttt
3841 ccctggagat caggttgccc ttttttggta gtctctccaa ttccctcctt cccggaagca
3901 tgtgacaatc aacaactttg tatacttaag ttcagtggac ctcaatttcc tcatctgtga
3961 aataaacggg actgaaaaat cattctggcc tcaagatgct ttgttgggt gtctaggtgc
4021 tccaggtgct tctgggagag gtgacctagt gagggatcag tgggaataga ggtgatattg
4081 tggggctttt ctggaaattg cagagaggtg catcgttttt ataatttatg aattttatg
4141 tattaatgtc atcctcctga tcttttcagc tgcattgggt aaatccttgc ctgccagagt
4201 gggtcagcgg tgagccagaa agggggctca ttctaacagt gctgtgtcct cctggagagt
4261 gccaactcat tctccaagta aaaaaagcca gatttgtggc tcacttcgtg gggaaatgtg
4321 tccagcgcac caacgcaggc gagggactgg gggaggaggg aagtgccctc ctgcagcacg
4381 cgaggttccg ggaccggctg gcctgctgga actcggccag gctcagctgc tccgcgctgg
4441 gcagccagga gcctgggccc cggggagggc ggtcccgggc ggcgcggtgg gccgagcgcg
4501 ggtcgcctcc ttgaggcggg cccgggcggg cggttgtat atcagggccg cgctgagctg
4561 cgccagctga ggtgtgagca gctgccgaag tcagttcctt gtggagccgg agctgggcgc
4621 ggattcgccg aggcaccgag gcactcagag gaggtgagag agcggcggca gacaacaggg
4681 gaccccgggc cggcggccca gagccgagcc aagcgtgccc gcgtgtgtcc ctgcgtgtcc
4741 gcgaggatgc gtgttcgcgg gtgtgtgctg cgttcacagg tgtttctgcg gcaggtgaat
4801 gacgggcgtg ggtcggtgcg cgctcggctt gcgcacacgg tgtctctaag tgcgcgggtg
4861 acgagggtcg ggatgtgccg gagaccccgg gcggagagcg ggattacaag tacaggaatc
4921 cctggccacg ctccccgccc ctggaaaccc agctggggcg aggggaggcg tggacgggac
4981 cgttctggga gctcgccttt ggctgcggtt ggctccaggc cccagcgca gtttgctcgc
5041 ggcgtgggga tgaagtccgt gtccctggag gggcccagga agggcgagga aagcggagtg
5101 gagtaagttc gtctaggatc ggtcccgggt ggctctggga tcc (SEQ ID NO: 1)
```

FIG. 2A

GenBank accession No. U24171

```
   1 gaattcaagg ccagcctggt ctacagagtg agttctagga cagccagaga aaacatgtgt
  61 tgaaaaaaaa aaaacaaaaa tcaatcaatc aatcttcaat gaatcaatcg atcactgaat
 121 cacacacgac ctagacagca agggccttcc ccttctccag ggctcactta cagttcccct
 181 ccctctcagt ggaggttaga caagattaca tgattgactc caacccatga aaccagcctt
 241 ctctacagtt agggcaaaag caaggattca cagaccgatg gtgtcactac actatggtag
 301 agctgctgtc agcctggacc cctgagagac cctgtgtgtg gagcagagtg tcccagaatt
 361 tatttgtgat agacaatgga gaagtaacct tgtgatgttt gttttatttt tttggttttt
 421 ggagacaggg ttcctctgtg tagctctggc tgtcctggaa ctcactttgt agaccaggct
 481 ggccttgaac tcagaaatcg cctgcctctg cctcccaagt gctgggatta aaggcttgtg
 541 ccacctcgcc tggctatttt gttttatttt cctgtcaatc caaacttgag ccacctggga
 601 caagggagcc tcagttgagg aatgctacc atgggcttgg cctgaaggca cgtctgtctg
 661 tgggtccttc ccttggttaa tggttaggac ctggctcact atctatcacc ccgaagcaag
 721 tgaacctgag tcctataaga aaaaaaggag ctgagggccc atgaaaagca agccagtaac
 781 caatgttctc taaagtccct gccttccagg ttcctgccct ggctttcctc agtgctggtt
 841 tgtgacctga aagtggaagg tgaaattaac cttttccttt ctaagacact tttggtcact
 901 gttttctcat agcaacagaa accctaaatg tggcattcac tgaactatct cgtcagctgg
 961 tctggctacc accttgtgtt tttgagggtc tgctagagcc tggagctcac tgaccaggtt
1021 aggtgcactg gccaggaagt cccttctagt ctcctgcttc cagtgcctca tgtgtgcctg
1081 tgcgtgcgtg cgtgtgtgtg tgtgtgtgtg tgtgtgtgtg tgtgtttgtg tgagtctata
1141 tgtgtgtgtg gcctatgtgt gtggtgtgtg catgcatgtg tgaatgtgtg tgcatgtttg
1201 tgtaagtctg tatatatgta tgtgtgtgtg tggtgtatgt gagtgtggtg tgtgtgtgta
1261 tgtgtgtgtg tgtgtattac aagagcatgc agcaagcctg gctctttcct gtgggtgatg
1321 ggatttcaac ttgggttcta tacttgcaag gcaaacaact ttaccagctg agcctcaaag
1381 gaatacattt ctaatgatgg agctgagact ggagaagttt tagaaatgtc agttctgatt
1441 tctcagggat atgaaaagct ctatcctgac cctcgtgctt agaccatttt ctattctctc
1501 tttgttttgt ggtcgaattt cttgggagtt tgtgtggagg tgacttcttc tgaaatctga
1561 cagtccctct ttggtactcc cctgtccttt tctggaagtg gtgattttgg cgtccacact
1621 tcctcttcct tcctgggtag cagcaacagc taaaatggag tcttccttat atctcccttg
1681 gtcccttgga tttcctttct atcagcccca gaggatacct tgcaaggctg catcagtcct
1741 cccatccctg gctgttgcct ctcggagacc agcagcaaaa tcggagctca gcaggcctgg
1801 gtctgttcag tcctgggtgg ggactagctt tctggccttc aggaacatgt cttgacatgt
1861 tcagccctgg aattgaagag gtggggctgc ttcagtgcag ggtggtggag acctgatgat
1921 acccaactac cagctgtggg gtgaggagga gcatgaatgg agacagagac cccagataat
1981 taaggacgtc ccactttgcc agcagaataa aaggtggtat gtatcttgtg acatgtatca
2041 ggtgaaggat gcttttgtgc atctgtgtgt gtgtgcctgg ggtgtgtatg tgtcaggtac
2101 tgtatgtagt cattttgtca ctttgtcatt ttggggtctg gagggctcct ccaaccatgt
2161 ttctgagtat acattcacgt gcaatggtgt gcctgactat acattcaagt gcaaggccaa
2221 gaatgtttgt tagaaagact gagtagtccc agacttaata aatatttgtt gagtacttt
2281 gtggtgctct gggaagccag aagttgttta aaataaatct ctccaacacc agtagggtaa
2341 aggcacagga ggtcacagca ctcagcagtt cagtataagc ctttattcaa gctgttttct
2401 cccaaagtaa acagacagac aatgtcactt ctatctgaga agcctgaggc caagggattt
2461 gggcagtttt gacatcctgt gctggcccct gacagcccag ccctggatgg acgacttgga
2521 tgcagggact ggaccgttca ggagctgggg cattgtggga gtggccatta tgtctgtcct
2581 ggtttggggg tctgaagggg gtccttcaac tgtgtttctg aacaggatga ggcttttgag
2641 gggggttggg aaggtggcca agcccttccc agacttccac cccccatcac agaagaggag
```

FIG. 2B

```
2701 gcctgtctag gtcagctaaa tccgaggagg aagactgggc atgtctgggc aggatctcta
2761 gacatcggag agcagatgtc agaactcaca gcttctccaa agcaggattt tgatctttta
2821 actaaagata tccgttcaaa ctaagactcc agtctctgct ttatttaaaa ttttgtttg
2881 tgtttgtttt gagagagaga ggaatttgtt tttgttttag aggcaggatg tatgtaacct
2941 tgatgaatta ttggtcctcc tgtttctgtc tcctgagtgc cgggattaca gatgtatgcc
3001 gctatcatct agatgatgcc ttactaggga tccaactcct ggcttcatac atgttaggca
3061 agcgctatat taacggagct acatcccttt ttggatgcat ggtgatctca gatagctcag
3121 gctagccttg agctccaaat ccccctgcc tcccgaagta ccgtgatttc aggcatgcac
3181 ctctatgctt agctgagatg gtggtcttgc tatgtagccc atgtgaccag gctggatcgt
3241 gtaacaagac tgaagaaaac ccccttctgc tgggtgtgat ggctcagacc tgtagtctta
3301 actctaagca aggaagttaa ggcaggaaga ttgccttgaa tatgagggcc accctgggct
3361 acatagcgag gcctcgtctc aaaagacccc aaacagaagg aaataaaact gactagagac
3421 atggaggaag gtgggaacgg agaatgtctt actgctatgt ctgtcaggaa catccgtaga
3481 tgtttctaga attgtcctt atcaatgtca ttttagtgga ctgtctggat cttgggaggg
3541 ggagtattag acatttccct cattttggac ccagagaaag aaatctgcaa gcagagtact
3601 ctggcagct tgccagaggc cagcaggtag ccattagtgt ggtcccagtc aggtcttgat
3661 gctctcactt gcaggatgta ttatggtgtg agaaatgttc acatgctggc ttctgaagag
3721 gggagagggg aggtaaggag cctggcggct gttttcttg gtagtccgtg gtctgagaat
3781 tggactcaat ctccccgatt tctgaggcgg ttgacagcat cctttccttc tgtggaactg
3841 ctttcctcgt ctgtgagaca gggaggaaat gatcgcgttc tggacccgat gtccgagggg
3901 cttctgggag gaggggggaaa aaaatctcca gacatagtgg gacttcttgg gattttaaac
3961 tattttttat tatttatggg cttgttttgt tttgagagg gtctcaatgg atagcccagg
4021 ctggtcttga acctgtaacg cccctcgtgc ctcaatctcc caagtatagg attccaggct
4081 tttgctatca tactcaaatg atcaatttat ttatatttga aacagtgtca catatttcaa
4141 gttggtctcc atcggaatag gtagctgtca aaacgaggtt gaatgcctat ttcccctcc
4201 tcaccccca ctggggctgt tattacagac gtgacccgca tgcccagttt atggggccct
4261 ggagctccaa cccagggctt cacttccagc aagttaggca aacactgtac caacagaccc
4321 acctcccgaa acccaggatt ttatttacta atatcagtga tctggaaaag agttagtcct
4381 tcccacagtt ggtcagggac agaccataa acactcactc agctctaact gtactgttgt
4441 tcatagatgt atgtggctct gctggtgcgc tgcgtgacaa gagaatagcc caggtgtggg
4501 ggagggagg gcgcgccctc ttaacgcgcg ccggttctag ctgtctggcg cgggcttaga
4561 ttcccagagg ggagggcggg ccagcgagtc cccgggatcg gtgaaggagt gggttggtcc
4621 tgcctctgag ggggcgggc ctggccgag ctataaggag gcagctcgac gccaactgca
4681 gcagccgaga ggtgtgagcc gccgcggtgt cagagtctag gggaattgga gtcaggcgca
4741 gatccacagc gatatccaga cattcagagg tgagagcttc gtggcaggga acaatagttc
4801 ttccccgtag caatgcgctg agcccagtgg gtgtccccag aagtgtgtgt gtgtgtgtgt
4861 gtgtgtgtgt ggtgatgagt ggatcacctg tgtgtgtata tgtgtatttg tcgtgcccg
4921 ccagagtcac aggtgtgtcc gcggcaggtg gatgacgggt gtgggtctga gcgtccgtgg
4981 tggctgaagg cttcgtttgt tggagt    (SEQ ID NO: 2)
//
```

Figure 3

```
  cgggatcg gtgaaggagt gggttggtcc tgcctctgag ggggcgggc ctgggccgag ctataaggag
gcagctcgac gccaactgca gcagccgaga ggtgtgagcc gccgcggtgt cagagtctag gggaattgga
gtcaggcgca gatccacagc gatatccaga cattcagagg tgagagcttc gtggcaggga acaatagttc
ttccccgtag ca  (SEQ ID NO: 3)
```

Figure 4

```
accattcccc tacccatgc tgctccaccg cactctgggg aggggctgg actgggcact cttgtccccc
aggctgagcc tccctccatc cctatgctgc ctgcttccca ggaacatgct tgggcagcag gctgtggctc
tgattggctt tctggccatc aggaacatgt cccaacatgt tgagctctgg catagaagag gctggtggct
attttgtcct tgggctgcct gttttcaggg aggaagggga tggtaggaga caggagacct ctaaagaccc
caggtaaacc ttagcctctt actctgaaca gggtatgtga tctgccagca ggatccttgc gacagggctg
ggatctgatg catgtgtgct tgtgtgagtg tgtgctggga gtcagattct gtgtgtgact tttaacagcc
tgctcccttg ccttcttcag ggcagaagtc ctcccttaga gtgtgtctgg gtacacattc aagtgcatgg
ttgcaaactt tttttttaa agcactgaat agtactagac acttagtagg tacttaagaa atattgaatg
tcgtggtggt ggtgagctag aagttataaa aaaaattctt tcccaaaaac aacaacaaaa agaattattt
cattgtgaag ctcagtacca caaaaattca ttacaataat tcattacaag cctttattaa aaaaaatttt
ctccccaaag taaacagaca gacaatgtct agtctatttg aaatgcctga aagcagaggg gcttcaaggc
agtgggagaa ggtgcctgtc ctctgctgga catttgacaa ccagccctttt ggatggtttg tatgtatagg
agcgaaggtg cagacagcag tggggcttag agtgggggtcc tgaggctgtg ctgtggccct tctggggttt
agccacaatc ctggcctgac tccagggcga ggcaggccaa gggggtctgc tgctgtgtcc tcccacccct
acctgggctc ccatccccac agcagaggag aaagaagcct gtcctccccg aggtcagctg cgttagagga
agaagactgg gcatgtctgg gcagagattt ccagactctg agcagcctga gatgtcagta attgtagctg
ctccaagcct gggttctgtt tttcagtggg atttctgttc agatgaacaa tccatcctct gcaattttt
aaaagcaaaa ctgcaaatgt ttcaggcaca gaaaggaggc aaaggtgaag tccaggggag gtcaggggtg
tgaggtagat gggagcggat agacacatca ctcatttctg tgtctgtcag aagaaccagt agacacttcc
agaattgtcc tttatttatg tcatctccat aaaccatctg caaatgaggg ttatttggca tttttgtcat
tttggaacca cagaaataaa ggatgacaag cagagagccc cgggcaggag gcaaaagtcc tgtgttccaa
ctatagtcat ttctttgctg catgatctga gttaggtcac cagacttctc tgagccccag tttccccagc
agtgtatacg ggctatgtgg ggagtattca ggagacagac aactcactcg tcaaatcctc cccttcctgg
ccaacaaagc tgctgcaacc acaggggttt cttctgttca ggtgagtgta gggtgtaggg agattggttc
aatgtccaat tcttctgttt ccctggagat caggttgccc tttttggta gtctctccaa ttccctcctt
cccggaagca tgtgacaatc aacaactttg tatacttaag ttcagtggac ctcaatttcc tcatctgtga
aataaacggg actgaaaaat cattctggcc tcaagatgct ttgttggggt gtctaggtgc tccaggtgct
tctgggagag gtgacctagt gagggatcag tgggaataga ggtgatattg tggggctttt ctggaaattg
cagagaggtg catcgttttt ataatttatg aatttttatg tattaatgtc atcctcctga tcttttcagc
tgcattgggt aaatccttgc ctgccagagt gggtcagcgg tgagccagaa aggggctca ttctaacagt
gctgtgtcct cctggagagt gccaactcat tctccaagta aaaaaagcca gatttgtggc tcacttcgtg
gggaaatgtg tccagcgcac caacgcaggc gagggactgg gggaggaggg aagtgccctc ctgcagcacg
cgaggttccg ggaccggctg gcctgctgga actcggccag gctcagctgc tccgcgctgg gcagccagga
gcctgggccc cggggagggc ggtcccgggc ggcgcggtgg gccgagcgcg ggtcgcctcc ttgaggcggg
cccggcggg gcggttgtat atcagggccg cgctgagctg cgccagctga ggtgtgagca gctgccgaag
tcagttcctt gtggagccgg agctgggcgc ggattcgccg aggcaccgag gcactcagag gaggcgcc
(SEQ ID NO: 4)
```

COMPOUNDS FOR ENHANCING P21 EXPRESSION AND METHODS OF USE THEREOF

This application asserts priority to U.S. Provisional Application No. 60/933,366, filed on Jun. 5, 2007, which is hereby incorporated by reference in its entirety.

The invention was also made with funds from New York State Department of Health, contract number CO19772. New York State has certain rights in this invention.

BACKGROUND OF THE INVENTION $p21^{cip1/waf1}$, is an important intermediate by which p53 mediates its role as an inhibitor of cellular proliferation in response to DNA damage. $p21^{cip1/waf1}$ may bind to and inhibit cyclin-dependent kinase activity, preventing the phosphorylation of critical cyclin-dependent kinase substrates and blocking cell cycle progression, and thus proliferation. Induction or overexpression of $p21^{cip1/waf1}$ leads to cell cycle inhibition and growth suppression in cells.

In many cells, $p21^{cip1/waf1}$ is increased in response to different types of stress, such as oxidative stress, x-ray radiation, and DNA damage. Oxidative stress is reported to be associated with numerous diseases and conditions, including stroke, hypoxia, ischemia, spinal cord injury and neurodegenerative conditions. Accordingly, compounds that enhance the expression of $p21^{cip1/waf1}$ and methods of identifying such compounds are beneficial for treating conditions and diseases that can be treated by enhancing expression of p21cip1/waf1 or by inhibiting cell cycle progression.

SUMMARY OF THE INVENTION

In one aspect, the present invention relates to a method for identifying a drug candidate for enhancing expression of $p21^{cip1/waf1}$ in a human patient suffering from a medical condition that can be treated by enhancing expression of $p21^{cip1/waf1}$. The method includes (a) providing a cell line comprising a nucleic acid sequence that comprises a $p21^{cip1/waf1}$ promoter operationally ligated to a reporter domain; (b) exposing the cell line to a compound; and (c) identifying a compound that induces expression of the reporter domain. The compound that induces expression of the reporter domain is a drug candidate for treating a medical condition that can be treated by enhancing expression of $p21^{cip1/waf1}$.

In another aspect, the invention relates to a method for enhancing expression of $p21^{cip1/waf1}$ in a human patient suffering from a medical condition that can be treated by enhancing expression of $p21^{cip1/waf1}$. The method includes administering to the patient an effective amount of one of the following compounds: ciclopirox olamine, dihydrocelastrol, colistimethate sodium, lycorine, diphenylurea, and acetylcysteine, chloroquine diphosphate, and 4'-methoxyflavone (acacetin).

BRIEF DESCRIPTION OF THE FIGURES

FIG. 1A. GenBank Accession No. U24170 (SEQ ID NO: 1) (nucleotide numbers 1-2460). Nucleotide sequence of human $p21^{cip1/waf1}$ gene.

FIG. 1B. GenBank Accession No. U24170 (SEQ ID NO: 1) (nucleotide numbers 2461-5143). Nucleotide sequence of human $p21^{cip1/waf1}$ gene.

FIG. 2A. GenBank Accession No. U24171 (SEQ ID NO: 2) (nucleotide numbers 1-2700). Nucleotide sequence of Mus musculus $p21^{cip1/waf1}$ gene.

FIG. 2B. GenBank Accession No. U24171 (SEQ ID NO: 2) (nucleotide numbers 2701-5006). Nucleotide sequence of Mus musculus $p21^{cip1/waf1}$ gene.

FIG. 3. 60 bp murine $p21^{cip1/waf1}$ promoter sequence from GenBank accession number U24171 (SEQ ID NO: 2). The sequence was sub-cloned in to pGL3 Luciferase Reporter Vector (Promega Corp. WI). Double underline represents an Sp1 binding site. Single underline represents TATA-box.

FIG. 4. 2,400 bp human $p21^{cip1/waf1}$ promoter sequence from GenBank accession number U24170 (SEQ ID NO: 1). The sequence was sub-cloned in to pGL3 Luciferase Reporter Vector (Promega Corp. WI). Double underline represents an Sp1 binding site. Single underline represents TATA-box.

METHOD FOR IDENTIFYING DRUG CANDIDATES

Figure 5:
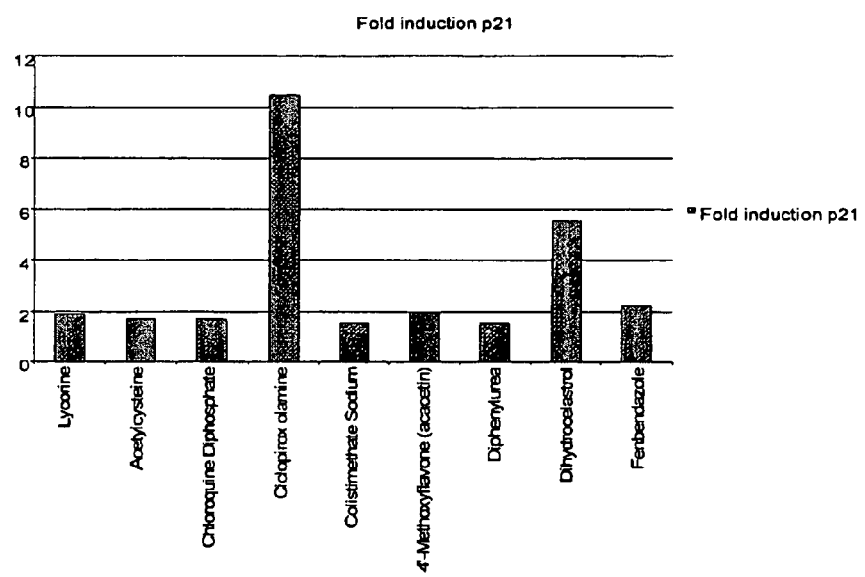
FIG. 5. Realtime PCR results. Cultured rat primary cortical neurons were treated with the respective drug for 12 hours. Neurons were harvested and RNA extracted using TriZol™ reagent (Invitrogen). cDNA was synthesized by standard reverse-transcriptase protocol. Realtime PCR performed using Applied Biosystems Realtime PCR cycler and rat p21-specific TaqMan primer and probe set. Data is displayed as fold induction relative to control (1-fold), which received vehicle only (no drug).

In one aspect of the invention, a method is provided for identifying a drug candidate for enhancing expression of $p21^{cip1/waf1}$ in human patients suffering from a medical condition that can be treated by enhancing expression of $p21^{cip1/waf1}$. The method includes providing a cell line comprising a nucleic acid sequence that comprises a $p21^{cip1/waf1}$ promoter operationally ligated to a reporter domain; exposing (treating) the cells to a chemical compound; and identifying a compound that induces expression of the reporter. The compound that induces expression of the reporter is a drug candidate for treating a medical condition that can be treated by (i.e., benefits from) enhancing expression of $p21^{cip1/waf1}$. Preferably, the compound that induces expression of the reporter is a drug candidate for treating a medical condition that inhibits cell cycle progression.

The $p21^{cip1/waf1}$ protein is also known as cyclin-dependent kinase inhibitor 1A (CDKN1A). The $p21^{cip1/waf1}$ expression can be enhanced in any cell that expresses p21 in the patient, and, most advantageously, in a damaged or injured cell.

As used herein, enhancing expression of $p21^{cip1/waf1}$ refers to increasing a level of measurable $p21^{cip1/waf1}$ in a given assay in the presence of a drug candidate relative to a measurable level of $p21^{cip1/waf1}$ in the absence of the drug candidate, when tested under the same conditions.

Expression of $p21^{cip1/waf1}$ is considered enhanced if expression under the same conditions is enhanced at least about 10% greater, preferably at least about 25% greater, more preferably at least about 50% greater, even more preferably at least about 75% greater, most preferably at least about 90% greater, or more than in the absence of the drug candidate.

Expression of $p21^{cip1/waf1}$ can be enhanced by any mechanism, and the invention is not limited to any particular mechanism. For example, expression of $p21^{cip1/waf1}$ can be enhanced by transcriptional induction of the cognate messenger RNA (mRNA) of $p21^{cip1/waf1}$ increased stability of $p21^{cip1/waf1}$ mRNA, increased translation of $p21^{cip1/waf1}$ mRNA into $p21^{cip1/waf1}$ increased stability of $p21^{cip1/waf1}$ increased $p21^{cip1/waf1}$ activity (in the presence or absence of increased protein), increased induction of $p21^{cip1/waf1}$ promoter activity, or any other mechanism.

Gene expression can be assessed by direct detection of protein product. Protein can be detected by methods known in the art, for example, by protein gel-electrophoresis or immunological methods. Protein can also be detected by detection of the corresponding mRNA products of transcription.

A drug candidate refers to a compound that may have activity in enhancing expression of p21$^{cip1/waf1}$ human patients in need thereof. The drug candidate may be identified for enhancing expression of p21$^{cip1/waf1}$ in any cell (in vitro) or mammal (in vivo).

Examples of cells in which the drug candidate enhances expression of p21$^{cip1/waf1}$ include neuronal cells (e.g., neurons, ganglia, Schwann cells, astrocytes, oligodendrocytes, and microglia), brain cells, spinal cord cells, kidney cells, intestinal cells, heart and cardiac muscle cells such as myocytes, skin cells, etc. Examples of mammals in which the drug candidate enhances expression of p21$^{cip1/waf1}$ include laboratory mammals, such as mice, rats, rodents, monkeys, baboons, etc.

A traditional paradigm for drug discovery and development typically involves three phases. During the early stages of drug discovery, large compound libraries of compounds (chemical molecules, biological molecules, small molecules, for example) are screened or tested in vitro for biological activity at a molecular target in order to identify potential new drugs, or lead compounds.

The active compounds, or hits, from this initial screening process are then tested through a series of other in vitro and in vivo tests to further characterize the active compounds. The in vivo tests at this phase may include tests in non-human mammals such as typical laboratory animals, for example, in mice, rats, rodents, monkeys, baboons, etc. If a compound meets the standards for continued development as a drug following in vitro and in vivo tests, the compound is typically selected for testing in humans.

A progressively smaller number of lead compounds at each stage are selected for testing in the next stage. The series of tests eventually leads to one or a few drug candidates being selected to proceed to testing in human clinical trials. The human clinical trials may include studies in a human suffering from a medical condition that can be treated by enhancing expression of p21$^{cip1/waf1}$.

Many drug candidates, however, fail to gain marketing approval by the U.S. Food and Drug Administration (FDA). Accordingly, the drug candidate as used herein is preferably, but not necessarily, approved by a governmental entity responsible for approving drugs (e.g., U.S. FDA) for use in a pharmaceutical.

Cell Line

A step in the method for identifying drug candidates is providing a cell line that includes a nucleic acid sequence that includes a p21$^{cip1/waf1}$ promoter operationally ligated to a reporter domain.

As used herein, a cell line refers to a population of cells capable of continuous or prolonged growth and division in vitro. Potentially any cell line that is capable of expressing a p21$^{cip1/waf1}$/reporter domain construct could be used for this screen. The cell line preferably has the properties of being immortalized and is capable of being replicated.

The cell line can be derived from any mammal, such as a mouse, rat, or human. Preferably, the cell line is derived from a human. Preferentially, the cell lines are neural. Some specific examples of cell lines include HT22 mouse hippocampal cell line, human cortical neuron cell line HCN-2, human cerebellum cell lines PFSK-1, D283 Med, and D341 Med, rat neuroblastoma cell line B35 and pheochromocytoma cell line PC12.

Preferably, the cell line includes cells that are capable of replicating a vector and expressing a heterologous gene encoded by a sequence in the vector. The vector optionally expresses a nucleic acid sequence that includes a p21$^{cip1/waf1}$ promoter/reporter domain construct.

A vector as used herein refers to a nucleic acid construct, generated recombinantly or synthetically, with a series of nucleic acid elements that permit transcription of a particular nucleic acid in a cell that hosts the vector. The vector can be part of a plasmid, virus, or nucleic acid fragment.

Any vector or plasmid DNA may be used as a backbone for carrying the nucleic acid sequence that comprises a p21$^{cip1/waf1}$ promoter operationally ligated to a reporter domain. Examples of suitable vectors include pGL3 vector (Promega, Madison, Wis.), pCAT3 vector (Promega, Madison, Wis.), and pSEAP2 Vector (Clontech).

Nucleic Acid Sequence

As stated above, the cell line includes a nucleic acid sequence that includes a p21$^{cip1/waf1}$ promoter operationally ligated to a reporter domain. Nucleic acid includes polyribonucleic acid (RNA) and polydeoxyribonucleic acid (DNA), both of which may be single-stranded or double-stranded.

The term operationally ligated refers to a linkage of nucleotide elements in a functional relationship. A nucleic acid sequence is "operationally ligated" when it is placed into a functional relationship with another nucleic acid sequence. For example, a promoter or enhancer is operationally ligated to a coding sequence if it affects the transcription of the coding sequence. The nucleic acid sequences that are operationally ligated are typically contiguous and, where necessary to join two protein coding regions, contiguous and in reading frame.

The term promoter refers to a nucleic acid sequence capable of initiating and controlling expression of a coding sequence or functional RNA. The wild-type p21$^{cip1/waf1}$ promoter is the promoter that is typically located upstream of (5' to) the p21$^{cip1/waf1}$ coding sequence. The sequence of full length wild-type p21$^{cip1/waf1}$ promoter is well-known in the art. See, for example, NCBI GenBank accession number U24170 (SEQ ID NO: 1), by 2141-4656, shown in FIG. 1. See also FIG. 4, which shows a 2,400 bp human p21$^{cip1/waf1}$ promoter sequence that was sub-cloned in to pGL3 Luciferase Reporter Vector (Promega Corp. WI).

The wild-type p21$^{cip1/waf1}$ promoter is approximately 2.4 kb in size. It typically contains a TATA box, two p53-binding sites and six conserved GC boxes that are binding sites for the transcription factor Sp1. The six conserved binding sites for Sp1 are known in the art as Sp1-1, Sp1-2, Sp1-3, Sp1-4, Sp1-5 and Sp1-6. The binding sites for Sp1-5 and Sp1-6 overlap. The promoter may include additional recognition or binding sites for other factors involved in regulation of transcription of the gene.

As used herein, the term p21$^{cip1/waf1}$ promoter refers to the full length wild-type p21$^{cip1/waf1}$ promoter or a truncated p21$^{cip1/waf1}$ promoter. The full length wild-type p21$^{cip1/waf1}$ promoter is described above.

A truncated p21$^{cip1/waf1}$ promoter has contiguous nucleotides removed from the 5' end of the full length wild-type p21$^{cip1/waf1}$ promoter, and must include at least a TATA box element. Truncated p21$^{cip1/waf1}$ promoters are well-known in the art. For example, a truncated p21$^{cip1/waf1}$ promoter may include a nucleic acid sequence of the full length wild-type p21$^{cip1/waf1}$ promoter that lacks contiguous nucleotides from the 5' end up to and including the two p53 binding sites (e.g., up to approximately −124 bp upstream, relative to the TATA box). Other examples include nucleic acid sequences of the full length wild-type p21$^{cip1/waf1}$ promoter that lack contiguous nucleotides from the 5' end up to and including the Sp1-1 site (e.g., up to approximately −110 bp upstream, relative to the TATA box), up to and including the Sp1-2 site (e.g., up to approximately −101 bp upstream, relative to the TATA box), up to and including the Sp1-3 site (e.g., up to approximately −70 bp upstream, relative to the TATA box), or up to and including the Sp1-4 site (e.g., up to approximately −60 bp upstream, relative to the TATA box).

Most preferably, the truncated $p21^{cip1/waf1}$ promoter contains −60 bp upstream, relative to the TATA box. Such a preferred truncated $p21^{cip1/waf1}$ promoter lacks the p53 binding sites and Sp1-1, Sp1-2, Sp1-3, and Sp-4 binding sites, but includes the Sp1-5 and Sp1-6 binding site and TATA box elements. See, for example, NCBI GenBank accession number U24171 (SEQ ID NO: 2), by 4593-4812, shown in FIG. 2. See also FIG. 3 which shows a 60 bp murine $p21^{cip1/waf1}$ promoter sequence that was sub-cloned into pGL3 luciferase reporter vector (Promega Corp., WI).

The full length wild-type $p21^{cip1/waf1}$ promoter necessarily encompasses regions of a truncated $p21^{cip1/waf1}$ promoter, described above. Accordingly, compounds that induce a truncated $p21^{cip1/waf1}$ promoter also induce the full length wild-type $p21^{cip1/waf1}$ promoter. However, compounds that induce the full length wild-type $p21^{cip1/waf1}$ promoter may not induce a truncated $p21^{cip1/waf1}$ promoter.

Therefore, in one embodiment, the method for identifying drug candidates further includes providing an additional cell line comprising a second nucleic acid sequence that comprises a $p21^{cip1/waf1}$ promoter operationally ligated to a reporter domain. For example, the method may include providing a first cell line that comprises a nucleic acid sequence that comprises a full length wild-type $p21^{cip1/waf1}$ promoter operationally ligated to a reporter domain, and a second cell line that comprises a nucleic acid sequence that comprises a truncated wild-type $p21^{cip1/waf1}$ promoter operationally ligated to a reporter domain. By providing more than one nucleic acid construct, a compound may be distinguished based on the mechanism (or binding site on the promoter) with which they induce expression of the reporter.

For purposes of the claimed invention, the $p21^{cip1/waf1}$ promoter may be derived from any mammal, e.g., a mouse, rat, or human. Preferably, the full length wild-type $p21^{cip1/waf1}$ promoter and cell line are derived from a human.

A reporter domain (or reporter) refers to a nucleic acid sequence that encodes a protein that is readily detectable, either by its presence or activity. The reporter domain is typically maintained under control of the promoter. Molecules used as reporters are well-known to one of skill in the art, and expression of a reporter domain in the cell-based reporter-gene assays may be detected by any technique well-known to one of skill in the art. Methods for detecting the expression of a reporter domain will vary with the reporter gene used.

Assays for the various reporter genes are well-known to one of skill in the art. For example, luciferase, beta-galactosidase ("b-gal"), beta-glucoronidase ("GUS"), beta-lactamase, chloramphenicol acetyltransferase ("CAT"), and alkaline phosphatase ("AP") are enzymes that can be analyzed in the presence of a substrate and could be amenable to high throughput screening. For example, the reaction products of luciferase, beta-galactosidase ("b-gal"), and alkaline phosphatase ("AP") are assayed by changes in light imaging (e.g., luciferase), spectrophotometric absorbance (e.g., b-gal), or fluorescence (e.g., AP). Assays for changes in light output, absorbance, and/or fluorescence are easily adapted for high throughput screening. For example, b-gal activity can be measured with a microplate reader. Green fluorescent protein ("GFP") activity can be measured by changes in fluorescence.

For example, in the case of mutant GFPs that fluoresce at 488 nm, standard fluorescence activated cell sorting ("FACS") equipment can be used to separate cells based upon GFP activity.

Alterations in the expression of a reporter gene may be determined by comparing the level of expression of the reporter gene to a negative control (e.g., PBS or another agent that is known to have no effect on the expression of the reporter gene) and optionally, a positive control (e.g., an agent that is known to have an effect on the expression of the reporter gene, preferably an agent that effects untranslated region-dependent expression). Alternatively, alterations in the expression of a reporter gene may be determined by comparing the level of expression of the reporter gene to a previously determined reference range.

Nucleic acid sequences that include a $p21^{cip1/waf1}$ promoter operationally ligated to a reporter domain are prepared by methods well-known in the art. The nucleic acid sequence can be incorporated into a vector or chromosomal DNA in the cells of the cell line.

Exposing the Cell to a Compound

Another step in the method for identifying drug candidates is exposing (treating) the cell to a compound. The term exposing refers to affecting an interaction or contact between the cell and compound, either directly or indirectly.

The cell can be exposed to a compound by any method. Suitable methods are known to those in the art. For example, the cell can be exposed to a compound by incubating the cell and compound in vitro.

The cell can also be exposed to the compound in vivo in a mammal, for example, in a laboratory mammal or in a human as part of clinical trials, as described above. The cell can be exposed to a compound in vivo by administering the compound to the mammal by methods known in the art, including the administration methods described below.

Identifying a Compound that Induces Expression of the Reporter

Another step in the method for identifying drug candidates is identifying a compound that induces expression of the reporter. A compound that induces expression of a reporter domain refers to a compound that is capable of increasing transcription or expression of a reporter gene.

The transcription or expression is increased relative to some base level of transcription or expression. The base level of transcription or expression is in the absence of the compound. Expression of the reporter is considered induced if the expression is increased by at least about 10%, preferably at least about 25%, more preferably at least about 50%, even more preferably at least about 75%, and most preferably at least about 90%, or more relative to some base level of transcription or expression.

A compound that activates a $p21^{cip1/waf1}$ promoter initiates expression of $p21^{cip1/waf1}$. Enhancing expression of $p21^{cip1/waf1}$ inhibits cell cycle progression because $p21^{cip1/waf1}$ is a key regulator of cell cycle entry, progression, and withdrawal. Therefore, a compound that induces expression of the reporter is a drug candidate for treating a medical condition that can be treated by (e.g., benefits from) inhibiting cell cycle progression.

The term treating or treated refers to relieving the condition by causing regression of the condition, preventing the condition from occurring in a mammal that may be predisposed to the condition, arresting the development of the condition, or ameliorating the condition or at least one symptom of the condition.

The term inhibiting cell cycle progression refers to slowing or preventing the process of passing through the cell cycle as compared to normal cells.

The term cell cycle progression refers to the process of passing through the different cell cycle phases. The cell cycle refers to the cyclic biochemical and structural events occurring during growth and division of cells. The phases of the cell cycle include $G_0$ (Gap 0; rest phase), G1 (Gap1), S phase (DNA synthesis), G2 (Gap 2), and M phase (mitosis).

Medical conditions in which inhibiting cell cycle progression is desired as a treatment include a wide variety of conditions. Examples include various cancers and leukemias, cardiovascular conditions, neurodegenerative diseases of the nervous system (described below), including stroke, spinal cord injury, trauma, insult to the central nervous system, Alzheimer's disease, Parkinson's disease, Huntington's chorea, amylotrophic lateral sclerosis, etc., and spinocerebellar degenerations. Further examples include medical conditions that can be treated by enhancing expression of $p21^{cip1/waf1}$.

A human patient suffering from a medical condition refers to a patient that has one or more symptoms of the stated medical condition or has a positive diagnosis based on one or more diagnostic tests.

Method for Enhancing $p21^{cip1/waf1}$ Expression

In another aspect, the invention relates to a method for enhancing expression of $p21^{cip1/waf1}$ protein in a human patient in need thereof. A patient in need thereof includes a patient suffering from a medical condition that can be treated by enhancing expression of $p21^{cip1/waf1}$. The method includes administering to the patient an effective amount of a compound selected from the group consisting of ciclopirox olamine, dihydrocelastrol, colistimethate sodium, lycorine, diphenylurea, and acetylcysteine, chloroquine diphosphate, and 4'-methoxyflavone (acacetin).

In another embodiment, the method includes administering to the patient an effective amount of a compound selected from the group consisting of ciclopirox olamine, dihydrocelastrol, colistimethate sodium, lycorine, diphenylurea, and acetylcysteine.

In yet another embodiment, the method includes administering to the patient an effective amount of a compound selected from the group consisting of chloroquine diphosphate and 4'-methoxyflavone (acacetin).

Method for Enhancing $p21^{cip1/waf1}$ Expression in Humans Suffering from Neurodegenerative Disease or Condition $p21^{cip1/waf1}$ protect cortical neurons from oxidative stress-induced death. $p21^{cip1/waf1}$ can also promote neurite remodeling and axonal regeneration. See, for example, Langley B, et al. Pulse inhibition of HDACs induces complete resistance to oxidative death in cortical neurons without toxicity and reveals a role for cytoplasmic $p21^{cip1/waf1}$ in cell cycle independent neuroprotection. *J. Neuroscience*. 28(1):163-176.

Accordingly, in another aspect, the human patient suffers from a neurodegenerative disease or condition. A neurodegenerative disease or condition typically refers to a disorder characterized by gradual and progressive loss of cells of the central or peripheral nervous system, which may lead to gradual and progressive loss of the corresponding tissue and/or organs. Examples of such cells include neurons, ganglia, Schwann cells, astrocytes, oligodendrocytes and microglia. Examples of corresponding tissue and organs include the brain and spinal cord.

For example, the neurodegenerative disease or condition can be an acute condition. Acute conditions generally occur as a result of trauma to a cell, tissue and/or organ of the nervous system. The trauma can, for example, partially or completely block blood flow to the cell, tissue and/or organ. Examples of acute neurodegenerative conditions include head injury and brain injury.

Alternatively, the neurodegenerative disease or condition can be a chronic neurodegenerative condition. Examples of chronic neurodegenerative diseases and conditions include Parkinson's disease, Alzheimer's disease, Huntington's disease and Amyotrophic Lateral Sclerosis (also known as Lou Gherig's disease).

Method for Enhancing $p21^{cip1/waf1}$ Expression in Humans Suffering from Stroke In a further aspect, the human patient suffers from the consequences of a stroke. Stroke generally involves the interruption of blood flow to and/or within the brain. The interruption of blood flow can be due to, for example, a blockage or rupture of an artery or vessel. The blockage typically occurs from a blood clot. As a result of the interruption of blood flow, the brain does not receive sufficient amounts of blood.

A loss of $p21^{cip1/waf1}$ increases the amount of damage that stroke causes to the brain. Accordingly, in one aspect of the invention, a method for enhancing expression of $p21^{cip1/waf1}$ in a human patient suffering from stroke is provided.

Method for Enhancing $p21^{cip1/waf1}$ Expression in Humans Suffering from Spinal Cord Injury In still a further aspect, the human patients suffer from spinal cord injury. Spinal cord injury refers to any damage to the spinal cord. The damage typically results in loss of function, such as mobility or feeling. Damage to the spinal cord can occur, for example, as a result or trauma (car accident, gunshot, falls, etc.) or disease (polio, spina bifida, Friedreich's Ataxia, etc).

Any injury to the spinal cord can be treated in accordance with the method of the present invention. For example, the injury can be a complete injury to the spinal cord. Complete injury typically refers to the lack of function (e.g., no sensation and no voluntary movement) below the site of injury. Both sides of the body are usually affected.

Alternatively, the injury may be an incomplete injury to the spinal cord. An incomplete injury generally refers to some function below the site of injury. For instance, a person with an incomplete injury may be able to move one limb more than another, may be able to feel parts of the body that cannot be moved, or may have more functioning on one side of the body than the other, etc.

Compounds

The drug candidate can be any chemical or biological molecule, including a small molecule. The drug candidate can be a salt of any such compounds.

A biological molecule is any molecule which contains a nucleic acid or amino acid sequence and has a molecular weight greater than 450. Examples of a biological molecule include nucleic acid molecules, oligonucleotides, oligopeptides, polypeptides, or proteins including antisense and dominant negative molecules; polypeptides, peptides, and proteins.

Small molecules include organic compounds, organometallic compounds, salts of organic and organometallic compounds, saccharides, amino acids, and nucleotides. Small molecules can further include molecules that would otherwise be considered biological molecules, except their molecular weight is not greater than 450. Thus, small molecules may be lipids, oligosaccharides, oligopeptides, and oligonucleotides, and their derivatives, having a molecular weight of 450 or less.

It is emphasized that small molecules can have any molecular weight. They are merely called small molecules because they typically have molecular weights less than 450. Small molecules include compounds that are found in nature as well as synthetic compounds.

Compounds useful in the methods of the present invention and processes to produce such compounds are known. For example, known compounds useful in the methods of the present invention preferably include ciclopirox olamine, dihydrocelastrol, colistimethate sodium, lycorine, diphenylurea, and acetylcysteine. Some additional compounds include chloroquine diphosphate and 4'-methoxyflavone (acacetin).

The compounds can be in the form of a pharmaceutically acceptable salt. The term "pharmaceutically acceptable salt" refers to a well-tolerated, nontoxic salt prepared from any one of the compounds mentioned above that have a basic and/or an acidic group, and an acid or base, respectively.

The acids may be inorganic or organic acids of any one of the compounds mentioned above. Examples of inorganic acids include hydrochloric, hydrobromic, nitric hydroiodic, sulfuric, and phosphoric acids. Examples of organic acids include carboxylic and sulfonic acids. The radical of the organic acids may be aliphatic or aromatic. Some examples of organic acids include formic, acetic, phenylacetic, propionic, succinic, glycolic, glucuronic, maleic, furoic, glutamic, benzoic, anthranilic, salicylic, phenylacetic, mandelic, embonic (pamoic), methanesulfonic, ethanesulfonic, panthenoic, benzenesulfonic, stearic, sulfanilic, alginic, tartaric, citric, gluconic, gulonic, arylsulfonic, and galacturonic acids.

Appropriate organic bases may be selected, for example, from N,N-dibenzylethylenediamine, chloroprocaine, choline, diethanolamine, ethylenediamine, meglumine (N-methylglucamine), and procaine.

Administration

The compounds are administered to a human patient suffering from a medical condition that can be treated by enhancing expression of $p21^{cip1/waf1}$ or by inhibiting cell cycle progression. The compound can be administered by any method known to those skilled in the art. Some examples of suitable modes of administration include systemic administration. Systemic administration can be enteral or parenteral, and preferably is oral administration. Liquid or solid formulations can be employed for systemic administration. Some suitable formulations include tablets, capsules, such as gelatin capsules, pills, troches, elixirs, suspensions, syrups, and wafers. Parenteral administration of the compound includes, for example, intravenous, intramuscular, and subcutaneous injections.

The compound is preferably in a suitable pharmaceutical composition comprising a pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols.

The pharmaceutical composition may also comprise one or more of the following: a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the compound.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent. Suitable salts include, for example, sodium or potassium chloride. Suitable buffers include, for example, mixtures of citric acid and sodium or potassium citrate, and sodium or potassium bicarbonate or biphosphate. Preferably, the buffering agent maintains the pH of the pharmaceutical composition in the range of about 5.5 to about 7.5. The salt and/or buffering agent is also useful to maintain the osmolality at a level suitable for administration to a mammal. Preferably the salt or buffering agent is present at a roughly isotonic concentration of about 150 mM to about 300 mM.

A compound may be administered to a mammal by controlled release, as is known in the art. Controlled release administration is a method of drug delivery to achieve a certain level of the drug over a particular period of time. Suitable controlled release formulations include delayed, sustained, and immediate (i.e., instantaneous) release. Methods for controlled release of drugs are well known in the art, and are described in, for example, U.S. Pat. Nos. 5,567,439; 6,838,094; 6,863,902; and 6,905,708, which are hereby incorporated by reference.

The compound is administered to the patient in an amount effective in achieving its purpose. For example, an effective amount may include an amount exposed to a cell that is sufficient to enhance expression of $p21^{cip1/waf1}$. The effective amount of the compound to be administered can be readily determined by those skilled in the art during pre-clinical trials and clinical trials by methods familiar to physicians and clinicians. Typical daily doses include approximately 1 mg to 1000 mg.

In one aspect, the compound is considered to be effective in enhancing $p21^{cip1/waf1}$ expression if the expression of $p21^{cip1/waf1}$ is enhanced by at least about 10%, preferably at least about 25%, more preferably at least about 50%, even more preferably at least about 75%, and most preferably at least about 90%. The $p21^{cip1/waf1}$ expression is considered enhanced relative to some base level of expression. The base level of expression is a level of induction that occurs in the absence of the compound.

The pharmaceutical composition may additionally contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anaesthetic agent such as for example a morphine derivative; or an isotonic agent etc., such as those described above. As a further precaution against oxidation or other spoilage, the compound may be stored under nitrogen gas in vials sealed with impermeable stoppers.

EXAMPLES

Example 1

A 2000 compound library was tested to identify drug candidates that enhance expression of $p21^{cip1/waf1}$. The library tested was The Sprectrum Collection™ from MicroSource Discovery System, Inc. (Groton, Conn.). The 2000 compounds in the library are primarily Food and Drug Administration (FDA)-approved compounds or natural products. An alphabetical list of the compounds is available at the MicroSource Discovery website at www.msdiscovery.com/spect.html, which is incorporated by reference. The compounds are supplied as 10 mM solutions in dimethyl sulfoxide (DMSO).

The library was screened using murine hippocampal HT22 cells transfected with a p21$^{cip1/waf1}$ promoter-luciferase construct. Compounds that induced expression of the reporter at a level approximately 2-fold above the base level were identified.

Example 2

In another analysis, realtime PCR was performed. Cultured rat primary cortical neurons were treated with the respective drug for 12 hours. Neurons were harvested and RNA extracted using TriZol™ reagent (Invitrogen). cDNA was synthesized by standard reverse-transcriptase protocol. Real-time PCR performed using Applied Biosystems Realtime PCR cycler and rat p21-specific TaqMan primer and probe set. Data is displayed as fold induction relative to control (1-fold), which received vehicle only (no drug). See FIG. 5.

Example 3

Based on available dosing data, rats were dosed with 1, 5, 10, 15 or 30 mg/kg ciclopirox (intraperiotoneal; 3 animals per concentration). Spinal cord, liver and skeletal muscle tissue was harvested 6-hours after drug delivery. Real-time rt-PCR was performed on RNA extracted from tissues to examine the expression of p21waf1/cip1, arginase-1, and VEGF in order to determine what might be the most efficacious dose.

Microarray gene analysis was also performed on spinal cord tissue RNA to determine gene expression changes that correlate with treatment and dose in an unbiased manner. These studies revealed that the arylhydrocarbon receptor (AHR) was a dose-dependent ciclopirox-regulated gene, in vivo, and provided confidence that ciclopirox could penetrate the blood brain barrier and could induce transcription in the spinal cord.

Results from these studies show that ciclopirox given as a single 30 mg/kg intraperiotoneal injection 30 minutes after a contusion injury at the level of T-8, can provide significant protection (reduced lesion volume). The effects of a single injection after injury on behavior showed little functional improvement.

Example 4

High Throughput Screen for p21 Activators

To identify novel activators of p21, fragments of the mouse or human p21 promoter were subcloned into the pGL3 basic promoter-reporter construct (see promoter sequence information). The resultant p21-luciferase reporter plasmids were each then stably transfected into a mouse hippocampal cell line, HT22. Several lines were generated and each showed predicted increases in p21-luciferase in response to the known p21 inducer trichostatin A (a HDAC inhibitor). Drugs were added to cells stably expressing p21-luciferase in a 96 well format. The HDAC inhibitor trichostatin A was used as a positive control. After 12 hours of drug treatment, the cells were lysed and luciferase activity was measured using a desktop luminometer. Cell viability was monitored in parallel, so that agents that induce toxicity can quickly be eliminated. Secondary screens including real time PCR or Western blots of p21 were monitored in primary neurons.

Example 5

Survival Assays—Oxidative Stress

Primary cortical neurons from E17 rat embryos were prepared according to a well-established papain dissociation method as described previously (Ratan, R. R., Murphy, T. H., Baraban, J. M. Oxidative stress induces apoptosis in embryonic cortical neurons. J Neurochem, 62, 376-379, (1994)). These neurons were plated on poly-D-lysine (Sigma) coated cell culture plates at a density of 1×106 cells/ml in minimal essential medium (MEM, Gibco BRL) with 5.5 g/l glucose, 10% FCS, 2 mM L-glutamine, 100 µM cysteine. 24 h after plating, neurons were rinsed with warm phosphate buffered saline and incubated with media containing HCA (2.5 or 5 mM). Control neurons were supplied media without HCA. In parallel, cortical neurons were co-treated with the "compounds/drugs" at the time of HCA exposure to evaluate neuronal protection. A concentration range was used to ensure a therapeutic dose. After incubation with treatment media for 24 h cells were assayed for viability. Calcein-acetoxymethy 1 ester (AM)/ethidium homodimer-1 staining (live/dead assay) (Molecular Probes, Eugene, Oreg.) under fluorescence microscopy and the MTT assay (3-(4,5-dimethylthiazol-2-yl)-2,5-diphenyltetrazolium bromide) (Promega, Madison, Wis.) methods were used as measures of cell viability and death. Testing of the compounds was performed in 48-well cell culture plates with 4-6 wells per treatment and repeated four times.

SEQUENCE LISTING

Incorporated herein by reference in its entirety is the attached Sequence Listing, which was created on Jun. 5, 2008.

What is claimed is:

1. A method for enhancing expression of p21$^{cip1/waf1}$ in a human patient suffering from a medical condition that can be treated by enhancing expression of p21$^{cip1/waf1}$, the method comprising administering to the patient an effective amount of a compound selected from a group consisting of dihydrocelastrol, colistimethate sodium, lycorine, diphenylurea and chloroquine diphosphate, wherein expression of p21$^{cip1/waf1}$ is enhanced in the patient suffering from a medical condition that can be treated by enhancing expression of p21$^{cip1/waf1}$.

2. The method according to claim 1, wherein the compound is selected from the group consisting of dihydrocelastrol, colistimethate sodium, lycorine, and diphenylurea.

3. The method according to claim 1, wherein the medical condition is spinal cord injury.

4. The method according to claim 1, wherein the medical condition is stroke, trauma, or insult to the central nervous system.

5. The method according to claim 1, wherein the medical condition is a neurodegenerative disease.

6. The method according to claim 1, wherein the neurodegenerative disease is Parkinson's disease, Alzheimer's disease, Huntington's disease or amyotrophic lateral sclerosis.

7. The method according to claim 1, wherein the compound is selected from the group consisting of dihydrocelastrol, colistimethate sodium, lycorine, and diphenylurea.

8. The method according to claim 1, wherein the compound is dihydrocelastrol.

9. The method according to claim 1, wherein the compound is chloroquine diphosphate.

10. The method according to claim 1, wherein the compound is colistimethate sodium.

11. The method according to claim 1, wherein the compound is lycorine.

12. The method according to claim 1, wherein the compound is diphenylurea.

13. A method for enhancing expression of $p21^{cip1/waf1}$ in a human patient suffering from a medical condition that can be treated by enhancing expression of $p21^{cip1/waf1}$, the method comprising administering to the patient an effective amount of colistimethate sodium, wherein expression of $p21^{cip1/waf1}$ is enhanced in the patient suffering from a medical condition that can be treated by enhancing expression of $p21^{cip1/waf1}$, wherein the medical condition is selected from the group consisting of spinal cord injury, stroke, trauma, Parkinson's disease, Alzheimer's disease, Huntington's disease and amyotrophic lateral sclerosis.

\* \* \* \* \*

SEQUENCE LISTING

```
<160> NUMBER OF SEQ ID NOS: 4

<210> SEQ ID NO 1
<211> LENGTH: 5143
<212> TYPE: DNA
<213> ORGANISM: Homo sapiens

<400> SEQUENCE: 1
ggatccctgt agagatgctc aggctgctga ggagggcgcg gtgcttggtc tctatgaata      60
cgatgaccta aagcaaaaaa agaagatggc tatgtcggtg aagctctatg gaactgggga     120
```

```
tcaggaggcc tggcagaaag gagtcctgtt tgcttctggg cagaacttgg catgatggag      180
acgccagcca gcgagatgat gccaaccaga tttgccgaaa ttattgagaa gaatctcaaa      240
agccgctagt agtaaaccga gtttcatatc agacccaggt cttggattga ggaacaggca      300
atgggatcat tcctcagtgt ggccaaagga tctgacgagc cctcagtctt cttggaaatt      360
cactacatag gcagccccaa tgcagacaaa ccaccccttg tttgttggga aggaattac       420 cttttgacagt ggtggtatct ccatcaaggc ttctgcaaat atggacctca tgagggccga     480
catgggagga gctacaacta tatgctcagc cattgtgtct gctgcaaatc tcagtttgcc     540
cattaatatt ataggtctgg cccctctgtg aaaacatgcc cagcggcaag gccaacaagc      600
tggggatgtt gttagagcca ggaacaggaa gaccatccag gttggtaaca ctgatgctga     660
ggggaggctc atactggctg atgcgctctg ttacgtgcac acatttaacc cgaaggtcat      720
cctcaatgcc accaccttaa caggtgtcat agatgtagct ttggggtcag gtgccactgg      780
ggtctttacc aattcatcct ggctctggaa caagctcttc gaggccagca ttgaaacagg      840
ggaccgtgtc tggaggatgc ctctcttcaa acattgtaca agacaggttg tagattgcca     900
gctggctgat gttaacaaca ttggaaaata tagatctgcg ggagcatgta catctgcggc      960
attcctgaaa gaattcgtga ctcatcctaa gtgggcacat ttagacatag caggtgtgat     1020
gaccaacaaa gatgaggttc cctatctatg gaaaggcatg accgggaggc ccacaaggac    1080
tctcatagag ttcttacttc gtttcagtca agacaatgct tagttcagat actcaaaaaa     1140
tgtcttcact ctgtcttaaa ttggacagtt gaagttaaaa ggttttttgaa tgaatggatg    1200 aaaatatttt aaaggaggca atttatattt aaaaatgtag aacacaatga aatttttatg    1260
ccttgatttt tttttcattt tacacaaaga tttatatatt ttttttttga gacggagtct     1320
cactctgtca cccaggctgg agtgcaggtg gcatgatctc agctcactgc aacctccgcc     1380
tcctaggttc aagcgattct cccacctcag ccacctgaat acctgggact acaggtgccc     1440
accaccatgc ccggctgatt tttgtatttt taatggagac ggggtttcac catattggcc     1500
aggctggtct caaaactcct gaccctgtga tctgcccgcc tcggcctccc aaagtgctgg    1560
gattacaggc gtaaaccacc acgcccggcc agtatatatt tttaattgag aagcaaaatt    1620
gtacttcaga tttgtgatgc taggaacatg agcaaactga aaattactaa ccacttgtca     1680
gaaacaataa atccaacttt ttgtgcaaaa aaaaaaaata caaatattag ctgggcatgg    1740
tggtgcatgc ctgtaatccc agctactcgg gaggctgagg cagaattgct tgaacctggg    1800
aggcggagac tgcagtgagc tgagattgtg ccactgctga ctttgtctca aaaacaaaa     1860 caaaacaaaa aaacaaaatg aaaacaaaaa gccagggctg cctctgctca ataatgttct    1920
atctttgttc cgcctcttct ctggggtctc acttcttggg agcctgtgtg aaggtgaatt    1980
cctctgaaag ctgactgccc ctatttggga ctccccagtc tctttctgag aaatggtgac    2040
attgttccca gcacttcctc tcccttccta ggcagcttct gcagccacca ctgagccttc    2100
ctcacatcct ccttcttcag gcttgggctt tccacctttc accattcccc taccccatgc    2160
tgctccaccg cactctgggg agggggctgg actgggcact cttgtccccc aggctgagcc    2220
tccctccatc cctatgctgc ctgcttccca ggaacatgct gggcagcag gctgtggctc    2280 tgattggctt tctggccatc aggaacatgt cccaacatgt tgagctctgg catagaagag    2340
gctggtggct attttgtcct tgggctgcct gttttcaggg aggaagggga tggtaggaga    2400
caggagacct ctaaagaccc caggtaaacc ttagcctctt actctgaaca gggtatgtga    2460
```

-continued

```
tctgccagca ggatccttgc gacagggctg ggatctgatg catgtgtgct tgtgtgagtg      2520
tgtgctggga gtcagattct gtgtgtgact tttaacagcc tgctcccttg ccttcttcag      2580
ggcagaagtc ctcccttaga gtgtgtctgg gtacacattc aagtgcatgg ttgcaaactt      2640
ttttttttaa agcactgaat agtactagac acttagtagg tacttaagaa atattgaatg      2700
tcgtggtggt ggtgagctag aagttataaa aaaaattctt tcccaaaaac aacaacaaaa      2760
agaattattt cattgtgaag ctcagtacca caaaaattca ttacaataat tcattacaag      2820
cctttattaa aaaaaatttt ctccccaaag taaacagaca gacaatgtct agtctatttg      2880
aaatgcctga agcagagggg cttcaaggc agtgggagaa ggtgcctgtc ctctgctgga      2940
catttgacaa ccagcccttt ggatggtttg tatgtatagg agcgaaggtg cagacagcag      3000 tgggcttag agtgggtcc tgaggctgtg ctgtggccct tctggggttt agccacaatc      3060
ctggcctgac tccagggcga ggcaggccaa ggggtctgc tgctgtgtcc tcccacccct      3120
acctgggctc ccatcccac agcagaggag aaagaagcct gtcctcccg aggtcagctg      3180 cgttagagga agaagactgg gcatgtctgg gcagagattt ccagactctg agcagcctga      3240
gatgtcagta attgtagctg ctccaagcct gggttctgtt tttcagtggg atttctgttc      3300
agatgaacaa tccatcctct gcaattttt aaaagcaaaa ctgcaaatgt tcaggcaca      3360 gaaaggaggc aaaggtgaag tccaggggag gtcaggggtg tgaggtagat gggagcggat      3420
agacacatca ctcatttctg tgtctgtcag aagaaccagt agacacttcc agaattgtcc      3480
tttatttatg tcatctccat aaaccatctg caaatgaggg ttatttggca ttttgtcat      3540 tttgaaacca cagaaataaa ggatgacaag cagagagccc cgggcaggag gcaaaagtcc      3600
tgtgttccaa ctatagtcat ttctttgctg catgatctga gttaggtcac cagacttctc      3660
tgagccccag tttccccagc agtgtatacg ggctatgtgg ggagtattca ggagacagac      3720
aactcactcg tcaaatcctc cccttcctgg ccaacaaagc tgctgcaacc acggggttt      3780 cttctgttca ggtgagtgta gggtgtaggg agattggttc aatgtccaat tcttctgttt      3840
ccctggagat caggttgccc ttttttggta gtctctccaa ttccctcctt cccggaagca      3900
tgtgacaatc aacaacttg tatacttaag ttcagtggac ctcaattccc tcatctgtga      3960
aataaacggg actgaaaaat cattctggcc tcaagatgct ttgttggggt gtctaggtgc      4020
tccaggtgct tctgggagag gtgacctagt gagggatcag tgggaataga ggtgatattg      4080
tggggctttt ctggaaattg cagagaggtg catcgttttt ataatttatg aattttttatg      4140 tattaatgtc atcctcctga tcttttcagc tgcattgggt aaatccttgc ctgccagagt      4200
gggtcagcgg tgagccagaa agggggctca ttctaacagt gctgtgtcct cctggagagt      4260
gccaactcat tctccaagta aaaaaagcca gatttgtggc tcacttcgtg gggaaatgtg      4320
tccagcgcac caacgcaggc gagggactgg gggaggaggg aagtgccctc ctgcagcacg      4380
cgaggttccg ggaccggctg gcctgctgga actcggccag gctcagctgc tccgcgctgg      4440
gcagccagga gcctgggccc cggggagggc ggtcccgggc ggcgcggtgg gccgagcgcg      4500
ggtcgcctcc ttgaggcggg cccgggcggg gcggttgtat atcagggccg cgctgagctg      4560
cgccagctga ggtgtgagca gctgccgaag tcagttcctt gtggagccgg agctgggcgc      4620
ggattcgccg aggcaccgag gcactcagag gaggtgagag agcggcggca gacaacaggg      4680
gaccccgggc cggcggccca gagccgagcc aagcgtgccc gcgtgtgtcc ctgcgtgtcc      4740
gcgaggatgc gtgttcgcgg gtgtgtgctg cgttcacagg tgtttctgcg gcaggtgaat      4800
gacgggcgtg ggtcggtgcg cgctcggctt gcgcacacgg tgtctctaag tgcgcgggtg      4860
```

```
acgagggtcg ggatgtgccg gagacccccgg gcggagagcg ggattacaag tacaggaatc    4920
cctggccacg ctccccgccc ctggaaaccc agctggggcg agggagggcg tggacgggac    4980
cgttctggga gctcgccttt ggctgcggtt ggctccaggc cccaggcgca gtttgctcgc    5040
ggcgtgggga tgaagtccgt gtccctggag gggcccagga agggcgagga aagcggagtg    5100
gagtaagttc gtctaggatc ggtcccgggt ggctctggga tcc                      5143
```

<210> SEQ ID NO 2
<211> LENGTH: 5006
<212> TYPE: DNA
<213> ORGANISM: Mus musculus

<400> SEQUENCE: 2

```
gaattcaagg ccagcctggt ctacagagtg agttctagga cagccagaga aacatgtgt       60 tgaaaaaaaa aaaacaaaaa tcaatcaatc aatcttcaat gaatcaatcg atcactgaat     120
cacacacgac ctagacagca agggccttcc ccttctccag ggctcactta cagttcccct     180
ccctctcagt ggaggttaga caagattaca tgattgactc caacccatga aaccagcctt     240
ctctacagtt agggcaaaag caaggattca cagaccgatg gtgtcactac actatggtag     300
agctgctgtc agcctggacc cctgagagac cctgtgtgtg gagcagagtg tcccagaatt     360
tatttgtgat agacaatgga gaagtaacct tgtgatgttt gttttatttt tttggttttt     420
ggagacaggg ttcctctgtg tagctctggc tgtcctggaa ctcactttgt agaccaggct     480
ggccttgaac tcagaaatcg cctgcctctg cctcccaagt gctgggatta aaggcttgtg     540
ccacctcgcc tggctatttt gttttatttt cctgtcaatc caaacttgag ccacctggga     600
caagggagcc tcagttgagg aatggctacc atgggcttgg cctgaaggca cgtctgtctg     660
tgggtccttc ccttggttaa tggttaggac ctggctcact atctatcacc ccgaagcaag     720
tgaacctgag tcctataaga aaaaaggag ctgagggccc atgaaaagca agccagtaac      780
caatgttctc taaagtccct gccttccagg ttcctgccct ggctttcctc agtgctggtt     840
tgtgacctga agtggaagg tgaaattaac cttttccttt ctaagacact tttggtcact      900
gttttctcat agcaacagaa accctaaatg tggcattcac tgaactatct cgtcagctgg     960
tctggctacc accttgtgtt tttgagggtc tgctagagcc tggagctcac tgaccaggtt    1020
aggtgcactg gccaggaagt cccttctagt ctcctgcttc cagtgcctca tgtgtgcctg    1080
tgcgtgcgtg cgtgtgtgtg tgtgtgtgtg tgtgtgtgtg tgtgtttgtg tgagtctata    1140
tgtgtgtgtg gcctatgtgt gtggtgtgtg catgcatgtg tgaatgtgtg tgcatgtttg    1200
tgtaagtctg tatatatgta tgtgtgtgtg tggtgtatgt gagtgtggtg tgtgtgtgta    1260
tgtgtgtgtg tgtgtattac aagagcatgc agcaagcctg gctctttcct gtgggtgatg    1320
ggatttcaac ttgggttcta tacttgcaag gcaaacaact ttaccagctg agcctcaaag    1380
gaatacattt ctaatgatgg agctgagact ggagaagttt tagaaatgtc agttctgatt    1440
tctcagggat atgaaaagct ctatcctgac cctcgtgctt agaccatttt ctattctctc    1500
tttgttttgt ggtcgaattt cttgggagtt tgtgtggagg tgacttcttc tgaaatctga    1560
cagtccctct ttggtactcc cctgtccttt tctggaagtg gtgattttgg cgtccacact    1620
tcctcttcct tcctgggtag cagcaacagc taaaatggag tcttccttat atctcccttg    1680
gtcccttgga tttccttcct atcagcccca gaggatacct tgcaaggctg catcagtcct    1740
cccatccctg gctgttgcct ctcggagacc agcagcaaaa tcggagctca gcaggcctgg    1800
```

-continued

```
gtctgttcag tcctgggtgg ggactagctt tctggccttc aggaacatgt cttgacatgt    1860
tcagccctgg aattgaagag gtggggctgc ttcagtgcag ggtggtggag acctgatgat    1920
acccaactac cagctgtggg gtgaggagga gcatgaatgg agacagagac cccagataat    1980
taaggacgtc ccactttgcc agcagaataa aaggtggtat gtatcttgtg acatgtatca    2040
ggtgaaggat gcttttgtgc atctgtgtgt gtgtgcctgg ggtgtgtatg tgtcaggtac    2100
tgtatgtagt cattttgtca ctttgtcatt ttggggtctg gagggctcct ccaaccatgt    2160
ttctgagtat acattcacgt gcaatggtgt gcctgactat acattcaagt gcaaggccaa    2220
gaatgtttgt tagaaagact gagtagtccc agacttaata aatatttgtt gagtactttt    2280
gtggtgctct gggaagccag aagttgttta aaataaatct ctccaacacc agtagggtaa    2340
aggcacagga ggtcacagca ctcagcagtt cagtataagc ctttattcaa gctgttttct    2400
cccaaagtaa acagacagac aatgtcactt ctatctgaga agcctgaggc caagggattt    2460
gggcagtttt gacatcctgt gctggcccct gacagcccag ccctggatgg acgacttgga    2520
tgcagggact ggaccgttca ggagctgggg cattgtggga gtggccatta tgtctgtcct    2580
ggtttggggg tctgaagggg gtccttcaac tgtgtttctg aacaggatga ggcttttgag    2640
gggggttggg aaggtggcca agcccttccc agacttccac cccccatcac agaagaggag    2700
gcctgtctag gtcagctaaa tccgaggagg aagactgggc atgtctgggc aggatctcta    2760
gacatcggag agcagatgtc agaactcaca gcttctccaa agcaggattt tgatctttta    2820
actaaagata tccgttcaaa ctaagactcc agtctctgct ttattttaaaa ttttttgtttg    2880
tgtttgtttt gagagagaga ggaatttgtt tttgttttag aggcaggatg tatgtaacct    2940
tgatgaatta ttggtcctcc tgtttctgtc tcctgagtgc cgggattaca gatgtatgcc    3000
gctatcatct agatgatgcc ttactaggga tccaactcct ggcttcatac atgttaggca    3060
agcgctatat taacggagct acatcccttt ttggatgcat ggtgatctca gatagctcag    3120
gctagccttg agctccaaat cccccctgcc tcccgaagta ccgtgatttc aggcatgcac    3180
ctctatgctt agctgagatg gtggtcttgc tatgtagccc atgtgaccag gctggatcgt    3240
gtaacaagac tgaagaaaac ccccttctgc tgggtgtgat ggctcagacc tgtagtctta    3300
actctaagca aggaagttaa ggcaggaaga ttgccttgaa tatgagggcc accctgggct    3360
acatagcgag gcctcgtctc aaaagacccc aaacagaagg aaataaaact gactagagac    3420
atggaggaag gtgggaacgg agaatgtctt actgctatgt ctgtcaggaa catccgtaga    3480
tgtttctaga attgtccttt atcaatgtca ttttagtgga ctgtctggat cttgggaggg    3540
ggagtattag acatttccct catttggac ccagagaaag aaatctgcaa gcagagtact    3600
ctgggcagct tgccagaggc cagcaggtag ccattagtgt ggtcccagtc aggtcttgat    3660
gctctcactt gcaggatgta ttatggtgtg agaaatgttc acatgctggc ttctgaagag    3720
gggagagggg aggtaaggag cctggcggct gttttttcttg gtagtccgtg gtctgagaat    3780
tggactcaat ctccccgatt tctgaggcgg ttgcacagcat cctttccttc tgtggaactg    3840
cttcctcgt ctgtgagaca gggaggaaat gatcgcgttc tggacccgat gtccgagggg    3900
cttctgggag gaggggggaaa aaaatctcca gacatagtgg gacttcttgg gatttttaaac    3960
tattttttat tatttatggg cttgttttgt ttttgagagg gtctcaatgg atagcccagg    4020
ctggtcttga acctgtaacg cccctcgtgc ctcaatctcc caagtatagg attccaggct    4080
tttgctatca tactcaaatg atcaatttat ttatatttga aacagtgtca catatttcaa    4140
gttggtctcc atcggaatag gtagctgtca aaacgaggtt gaatgcctat ttccccctcc    4200
```

-continued

| | |
|---|---|
| tcacccccca ctggggctgt tattacagac gtgacccgca tgcccagttt atggggccct | 4260 |
| ggagctccaa cccagggctt cacttccagc aagttaggca aacactgtac caacagaccc | 4320 |
| acctcccgaa acccaggatt ttatttacta atatcagtga tctggaaaag agttagtcct | 4380 |
| tcccacagtt ggtcagggac agacccataa acactcactc agctctaact gtactgttgt | 4440 |
| tcatagatgt atgtggctct gctggtgcgc tgcgtgacaa agaatagcc caggtgtggg | 4500 |
| ggaggggagg gcgcgccctc ttaacgcgcg ccggttctag ctgtctggcg cgggcttaga | 4560 |
| ttcccagagg ggagggcggg ccagcgagtc cccgggatcg gtgaaggagt gggttggtcc | 4620 |
| tgcctctgag ggggcgggc ctgggccgag ctataaggag gcagctcgac gccaactgca | 4680 |
| gcagccgaga ggtgtgagcc gccgcggtgt cagagtctag gggaattgga gtcaggcgca | 4740 |
| gatccacagc gatatccaga cattcagagg tgagagcttc gtggcaggga acaatagttc | 4800 |
| ttccccgtag caatgcgctg agcccagtgg gtgtccccag aagtgtgtgt gtgtgtgtgt | 4860 |
| gtgtgtgtgt ggtgatgagt ggatcacctg tgtgtgtata tgtgtatttg tgcgtgcccg | 4920 |
| ccagagtcac aggtgtgtcc gcggcaggtg gatgacgggt gtgggtctga gcgtccgtgg | 4980 |
| tggctgaagg cttcgtttgt tggagt | 5006 |

<210> SEQ ID NO 3
<211> LENGTH: 220
<212> TYPE: DNA
<213> ORGANISM: Artificial Sequence
<220> FEATURE:
<223> OTHER INFORMATION: Synthetic nucleotide sequence

<400> SEQUENCE: 3

| | |
|---|---|
| cgggatcggt gaaggagtgg gttggtcctg cctctgaggg ggcggggcct gggccgagct | 60 |
| ataaggaggc agctcgacgc caactgcagc agccgagagg tgtgagccgc cgcggtgtca | 120 |
| gagtctaggg gaattggagt caggcgcaga tccacagcga tatccagaca ttcagaggtg | 180 |
| agagcttcgt ggcagggaac aatagttctt ccccgtagca | 220 |

<210> SEQ ID NO 4
<211> LENGTH: 2518
<212> TYPE: DNA
<213> ORGANISM: Artificial Sequence
<220> FEATURE:
<223> OTHER INFORMATION: Synthetic nucleotide sequence

<400> SEQUENCE: 4

| | |
|---|---|
| accattcccc tacccatgc tgctccaccg cactctgggg aggggggctgg actgggcact | 60 |
| cttgtccccc aggctgagcc tccctccatc cctatgctgc ctgcttccca ggaacatgct | 120 |
| tgggcagcag gctgtggctc tgattggctt tctggccatc aggaacatgt cccaacatgt | 180 |
| tgagctctgg catagaagag gctggtggct attttgtcct tgggctgcct gttttcaggg | 240 |
| aggaagggga tggtaggaga caggagacct ctaaagaccc caggtaaacc ttagcctctt | 300 |
| actctgaaca gggtatgtga tctgccagca ggatccttgc gacagggctg ggatctgatg | 360 |
| catgtgtgct tgtgtgagtg tgtgctggga gtcagattct gtgtgtgact tttaacagcc | 420 |
| tgctccttg ccttcttcag ggcagaagtc ctcccttaga gtgtgtctgg gtacacattc | 480 |
| aagtgcatgg ttgcaaactt tttttttttaa agcactgaat agtactagac acttagtagg | 540 |
| tacttaagaa atattgaatg tcgtggtggt ggtgagctag aagttataaa aaaaattctt | 600 |
| tcccaaaaac aacaacaaaa agaattattt cattgtgaag ctcagtacca caaaattca | 660 |

-continued

```
ttacaataat tcattacaag cctttattaa aaaaaatttt ctccccaaag taaacagaca    720
gacaatgtct agtctatttg aaatgcctga aagcagaggg gcttcaaggc agtgggagaa    780
ggtgcctgtc ctctgctgga catttgacaa ccagcccttt ggatggtttg tatgtatagg    840
agcgaaggtg cagacagcag tggggcttag agtggggtcc tgaggctgtg ctgtggccct    900
tctggggttt agccacaatc ctggcctgac tccagggcga ggcaggccaa ggggtctgc     960
tgctgtgtcc tcccacccct acctgggctc ccatccccac agcagaggag aaagaagcct   1020
gtcctccccg aggtcagctg cgttagagga agaagactgg gcatgtctgg gcagagattt   1080
ccagactctg agcagcctga gatgtcagta attgtagctg ctccaagcct gggttctgtt   1140
tttcagtggg atttctgttc agatgaacaa tccatcctct gcaattttt aaaagcaaaa    1200
ctgcaaatgt ttcaggcaca gaaaggaggc aaaggtgaag tccaggggag gtcagggtg    1260
tgaggtagat gggagcggat agacacatca ctcatttctg tgtctgtcag aagaaccagt   1320
agacacttcc agaattgtcc tttatttatg tcatctccat aaaccatctg caaatgaggg   1380
ttatttggca tttttgtcat tttggaacca cagaaataaa ggatgacaag cagagagccc   1440
cgggcaggag gcaaaagtcc tgtgttccaa ctatagtcat ttctttgctg catgatctga   1500
gttaggtcac cagacttctc tgagccccag tttccccagc agtgtatacg ggctatgtgg   1560
ggagtattca ggagacagac aactcactcg tcaaatcctc cccttcctgg ccaacaaagc   1620
tgctgcaacc acagggggttt cttctgttca ggtgagtgta gggtgtaggg agattggttc   1680
aatgtccaat tcttctgttt ccctggagat caggttgccc ttttttggta gtctctccaa   1740
ttccctcctt cccggaagca tgtgacaatc aacaactttg tatacttaag ttcagtggac   1800
ctcaatttcc tcatctgtga aataaacggg actgaaaaat cattctggcc tcaagatgct   1860
ttgttggggt gtctaggtgc tccaggtgct tctgggagag gtgacctagt gagggatcag   1920
tgggaataga ggtgatattg tggggctttt ctggaaattg cagagaggtg catcgttttt   1980
ataatttatg aattttatg tattaatgtc atcctcctga tcttttcagc tgcattgggt    2040
aaatccttgc ctgccagagt gggtcagcgg tgagccagaa aggggctca ttctaacagt    2100
gctgtgtcct cctggagagt gccaactcat tctccaagta aaaaaagcca gatttgtggc   2160
tcacttcgtg gggaaatgtg tccagcgcac caacgcaggc gagggactgg gggaggaggg   2220
aagtgccctc ctgcagcacg cgaggttccg ggaccggctg gcctgctgga actcggccag   2280
gctcagctgc tccgcgctgg gcagccagga gcctgggccc cggggagggc ggtcccgggc   2340
ggcgcggtgg gccgagcgcg ggtcgcctcc ttgaggcggg cccggcggg gcggttgtat    2400
atcagggccg cgctgagctg cgccagctga ggtgtgagca gctgccgaag tcagttcctt   2460
gtggagccgg agctgggcgc ggattcgccg aggcaccgag gcactcagag gaggcgcc    2518
```